(12) United States Patent
Zuchner et al.

(10) Patent No.: US 7,811,762 B2
(45) Date of Patent: Oct. 12, 2010

(54) IDENTIFICATION OF A NOVEL GENE UNDERLYING FAMILIAL SPASTIC PARAPLEGIA

(75) Inventors: Stephan Zuchner, Pinecrest, FL (US); Margaret Pericak-Vance, Coral Gables, FL (US); Allison Ashley-Koch, Cary, NC (US); Corey Braastad, Southampton, MA (US); Narasimhan Nagan, South Grafton, MA (US); Hui Zhu, Belmont, MA (US); Jeffrey G. Jones, Wilbraham, MA (US)

(73) Assignee: Duke University, Durham, NC (US)

( * ) Notice: Subject to any disclaimer, the term of this patent is extended or adjusted under 35 U.S.C. 154(b) by 541 days.

(21) Appl. No.: 11/729,422

(22) Filed: Mar. 28, 2007

(65) Prior Publication Data

US 2007/0248974 A1 Oct. 25, 2007

Related U.S. Application Data

(60) Provisional application No. 60/788,450, filed on Mar. 30, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................... 435/6; 435/91.2; 536/23.1; 536/24.3

(58) Field of Classification Search ........................ None
See application file for complete search history.

(56) References Cited

U.S. PATENT DOCUMENTS

| 6,924,126 | B1 | 8/2005 | Weissenbach et al. |
| 7,108,925 | B2 | 9/2006 | Campbell |
| 2003/0224968 | A1 | 12/2003 | Fink et al. |
| 2005/0266479 | A1 | 12/2005 | Weissenbach et al. |
| 2006/0057640 | A1 | 3/2006 | Matsunami et al. |
| 2006/0073478 | A1 | 4/2006 | Fink et al. |
| 2007/0015202 | A1 | 1/2007 | Fink et al. |

OTHER PUBLICATIONS

Ashley-Koch, A., et al., "Fine Mapping and Genetic Heterogeneity in the Pure Form of Autosomal Dominant Familial Spastic Paraplegia," *Neurogenetics*, 3:91-97 (2001).
Evans, K., et al., "Interaction of Two Hereditary Spastic Paraplegia Gene Products, Spastin and Atlastin, Suggests a Common Pathway for Axonal Maintenance," *PNAS*, 103:10666-10671 (2006).
Fink, J.K., et al., "Hereditary Spastic Paragplegia: Genetic Heterogeneity and Genotype-Phenotype Correlation," *Seminars in Neurology*, 19:301-309 (1999).
Fortini, D., et al., "Current Insights Into Familial Spastic Paraparesis: New Advances in an Old Disease," *Functional Neurology*, 18:43-49 (2003).
Hansen, J.J., et al., "Hereditary Spastic Paraplegia SPG13 is Associated with a Mutation in the Gene Encoding the Mitochondrial Chaperonin Hsp60," *Am. J. Hum. Genet.*, 70:1328-1332 (2002).
Hazan, J. et al., "Spastin, a New AAA Protein, is Altered in the Most Frequent Form of Autosomal Dominant Spastic Paraplegia," *Nat. Genet.* 23:296-303 (1999).
Hentati, A., et al. "Linkage of a Locus for Autosomal Dominant Familial Spastic Paraplegia to Chromosome 2p Markers," *Human Molecular Genetics*, 3:1867-1871 (1994).
Hiltunen, M., et al., "Butyrylcholinesterase K. Variant and Apolipoprotein E4 Genes to Not Act in Synergy in Finnish Late-Onset Alzheimer's Disease Patients," *Neuroscience Letters*, 250:69-71 (1998).
Ishikawa, K. et al., "An Autosomal Dominant Cerebellar Ataxia Linked to Chromosome 16q22.1 Is Associated with A Single-Nucleotide Substitution in the 5' Untranslated Region of the Gene Encoding a Protein Spectrin Repeat and Rho Guanine-Nucleotide Exchange-Factor Domains," *Am. J. Hum. Genet.* 77:280-296 (2005).
Orlacchio, A., "New Locus for Hereditary Spastic Paraplegia Maps to Chromosome 1p31.1-1p21.1," *Ann. Neurol.* 58:423-429 (2005).
Raskind, W.H., et al., "Familial Spastic Paraparesis: Evaluation of Locus Heterogeneity, Anticipation, and Haplotype Mapping of the SPG4 Locus on the Short Arm of Chromosome 2," *Am. J. Med. Genet.*, 74:26-36 (1997).
Reid, E., et al., A Kinesin Heavy Chain (KIF5A) Mutation in Hereditary Spastic Paraplegia (SPG10), *Am. J. Hum. Genet.* 71:1189-1194 (2002).
Reid, E., et al., "A New locus for Autosomal Dominant "Pure" Hereditary Spastic Paraplegia Mapping to Chromosome 12q13, and Evidence for Further Genetic Heterogeneity," *Am. J. Hum. Genet.* 65:757-763 (1999).
Reid, E., "Science in Motion: Common Molecular Pathological Themes Emerge in the Hereditary Spastic Paraplegias," *J. Med. Genet.*40: 81-86 (2003).
Scott, W.K. et al., "Locus Heterogeneity, Anticipation and Reduction of the Chromosome 2p Minimal Candidate Region in Autosomal Dominant Familial Spastic Paraplegia," *Neurogenetics*, 1:95-102 (1997).
Svenson, I.K., et al., "Identification and Expression Analysis of Spastin Gene Mutations in Hereditary Spastic Paraplegia," *Am. J. Hum. Genet.* 68:1077-1085 (2001).
Svenson, I.K., et al., Intragenic Modifiers of Hereditary Spastic Paraplegia Due to Spastin Gene Mutations, *Neurogenetics* 5:157-164 (2004).
Tallaksen, C.M.E., et al., "Recent Advances in Hereditary Spastic Paraplegia," *Curr. Opinion in Neurology*, 14:457-463 (2001)
Züchner, S., et al. "A New Locus for Dominant Hereditary Spastic Paraplegia Maps to Chromosome 2p12," *Neurogenetics*, 7:127-129 (2006)..

(Continued)

*Primary Examiner*—Teresa E Strzelecka
(74) *Attorney, Agent, or Firm*—Hamilton, Brook, Smith & Reynolds, P.C.

(57) ABSTRACT

Methods of identifying polymorphisms associated with hereditary spastic paraplegia (SPG), are described. The polymorphisms associated with SPG include specific mutations in the receptor expression enhancing protein 1 (REEP1) gene. Also described are methods of diagnosis of SPG.

20 Claims, No Drawings

OTHER PUBLICATIONS

Züchner, S., et al. "Mutations in the Novel Mitochondrial Protein REEP1 Cause Hereditary Spastic Paraplegia Type 31" *Am. J. Hum. Genet.* 79:365-369 (2006).

Zhao, X., et al. "Mutations in a Newly Identified GTPase Gene Cause Autosomal Dominant Hereditary Spastic Paraplegia," *Nature Genetics*, 29: 326-331 (2001).

Finsterer, J., "Hereditäre Spastische Paraplegien," *Nervenarzt*, 74:497-504 (2003).

Saito, H., et al., "RTP Family Members Induce Functional Expression of Mammalian Odorant Receptors," *Cell*, 119:679-691 (2004).

Database SNPDB, NCBI: "Single Nucleotide Polymorphism," Accession No. rs3087642 (2002).

IDENTIFICATION OF A NOVEL GENE UNDERLYING FAMILIAL SPASTIC PARAPLEGIA

RELATED APPLICATION

This application claims the benefit of U.S. Provisional Application No. 60/788,450, filed on Mar. 30, 2006. The entire teachings of the above application are incorporated herein by reference.

GOVERNMENT SUPPORT

The invention was supported, in whole or in part, by grant P01 NS26630 from the National Institutes of Health. The Government has certain rights in the invention.

BACKGROUND OF THE INVENTION

Hereditary spastic paraplegias (SPG) are a group of neurodegenerative diseases clinically characterized by progressive lower limb spasticity, hyperreflexia, and paresis. SPG may be inherited in an autosomal dominant, autosomal recessive, or X-linked recessive manner, with the majority presenting as autosomal dominant SPG (Fink, J. K. and Hedera, P., Semin. Neurol. 19(3):301-9 (1999); Tallaksen, C. M. et al., Curr. Opin. Neurol. 14(4):457-63 (2001)). Eleven different chromosomal loci have been identified for autosomal dominant SPG (Reid, E., J. Med. Genet. 40, 81-86 (2003); Orlacchio, A. et al., Ann. Neurol. 58, 423-429 (2005). Five genes underlying autosomal dominant SPG have been discovered: spastin (Hazan, J. et al., Nat. Genet. 23:296-303 (1999)); atlastin (Zhao, X. et al., Nat. Genet. 29:326-331 (2001)); HSP60 (Hansen, J. J. et al., Am. J. Hum. Genet. 70:1328-1332 (2002)); KIF5A (Reid, E. et al., Am. J. Hum. Genet. 71:1189-1194 (2002)); and BSCL2 (Hiltunen, M. et al., Neurosci. Let. 250:69-71 (1998)). Further genetic heterogeneity has been suggested (Ashley-Koch, A. et al., Neurogenetics. 3:91-97 (2001)). A need remains for means to distinguish the variants of SPG from one another.

SUMMARY OF THE INVENTION

The present invention is drawn to methods of assessing an individual for the presence or absence of a genetic polymorphism associated with hereditary spastic paraplegia (SPG). In the methods of the invention, a test sample from the individual is assessed for the presence of at least one mutation in the receptor expression enhancing protein 1 (REEP1) gene. Assessing the test sample can be performed by standard methods that may include amplification of all or a fragment of the REEP1 gene, and/or direct sequence analysis. The test sample comprises nucleic acids, such as genomic DNA (e.g., genomic DNA comprising chromosome 2 or a fragment thereof comprising 2p12). The mutation of interest can be, for example, selected from the group consisting of: a single base transversion C→G at nucleotide 56; a single base transition C→A at nucleotide 59; a transition at nucleotide 182-2G→A; a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14; a single base transition G→T in the 3'-UTR at 606+43; or a single base transition G→A in the 3'-UTR at 606+50. The presence of at least one mutation in the REEP1 gene is indicative of the presence of a genetic polymorphism associated with hereditary spastic paraplegia.

The methods of the invention additionally include methods of diagnosing hereditary spastic paraplegia (SPG) in an individual, by assessing a test sample from the individual for the presence of at least one mutation in the REEP1 gene of the individual, as described above. The presence of a mutation in the REEP1 gene is indicative of hereditary spastic paraplegia. The invention further pertains to kits useful in the methods of the invention.

The methods of the invention provide simple means to distinguish a particular type of hereditary spastic paraplegia from other types, as well as to identify those who are affected with the disease.

DETAILED DESCRIPTION OF THE INVENTION

The present invention provides methods of assessing individuals for the presence or absence of a genetic polymorphism associated with hereditary spastic paraplegia (SPG), as well as methods of diagnosing SPG in an individual, and methods of assessing an individual for carrier status for SPG. As described herein, Applicant has identified certain mutations of interest in the receptor expression enhancing protein 1 (REEP1) gene that are associated with SPG. The mutations in the REEP1 gene described herein are alterations (e.g., deletions, insertions, or transitions) in the nucleic acid sequence of the REEP1 gene. The position of the mutations in the sequence of REEP1 are numbered in relation to the mRNA or cDNA sequence: that is, the numbered position of an altered nucleotide is the number of that nucleotide in the mRNA or cDNA sequence. The mRNA sequence associated with the REEP1 gene is set forth in GenBank accession number AY562239, as submitted on Nov. 26, 2004 (shown as SEQ ID NO: 1 in the sequence listing). The mutations of interest include the following alterations a single base transversion C→G at nucleotide 56; a single base transition C→A at nucleotide 59; a transition at nucleotide 182-2G→A; a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14; a single base transition G→T in the 3'-UTR at 606+43; or a single base transition G→A in the 3'-UTR at 606+50.

As a result of this discovery, methods are now available to assess an individual for the presence of a genetic polymorphism associated with SPG, as well as methods for diagnosing SPG in an individual. In the methods of the invention, a test sample from an individual is assessed for the presence of one or more polymorphisms in the REEP1 gene (herein also referred to as the "polymorphisms of interest" or "polymorphisms associated with SPG"). The individual is a human individual, and may be of any race and any age, including fetus, infant, juvenile, adolescent, and adult. Representative individuals include those who have not previously been diagnosed as having SPG, as well as those who have been determined to be at risk for having SPG, and those who have been initially diagnosed as being affected by SPG, where confirming information is desired.

The test sample is a sample containing nucleic acids comprising the REEP1 gene or a fragment of the REEP1 gene, REEP1 mRNA or a fragment of REEP1 mRNA, REEP1 cDNA or a fragment of REEP1 cDNA, from the individual. The term, "fragment," as used herein, indicates that the portion of the gene, mRNA or cDNA is a polynucleotide of a length that is sufficient to identify it as a fragment of REEP1: in a representative embodiment, a fragment comprises one or more exons of the REEP1 gene; in another representative embodiment, a fragment comprises part of an exon of the REEP1 gene. The fragment can also include intron/exon junction(s) of the REEP1 gene, and/or the 5'-UTR or 3'-UTR.

The test sample is prepared from a biological sample from the individual. The biological sample can be a sample from any source which contains genomic DNA (e.g., chromosomal nucleic acids) or RNA, such as a blood sample, sample of amniotic fluid, sample of cerebrospinal fluid, or tissue sample from skin, muscle, buccal or conjunctival mucosa, placenta, gastrointestinal tract or other organs. A biological sample of nucleic acid from fetal cells or tissue can be obtained by appropriate methods, such as by amniocentesis or chorionic villus sampling (direct or cultured). In certain embodiments, a biological sample containing genomic DNA comprising chromosome 2 or a fragment thereof (e.g., a fragment comprising 2p12, or a fragment comprising one or more exons of the REEP1 gene) is used. A biological sample can be used as the test sample; alternatively, a biological sample can be processed to enhance access to nucleic acids, or copies of nucleic acids (e.g., copies of nucleic acids comprising the REEP1 gene), and the processed biological sample can then be used as the test sample. For example, in one embodiment, cDNA is prepared from a biological sample comprising mRNA, for use in the methods. Alternatively or in addition, if desired, an amplification method can be used to amplify nucleic acids comprising all or a fragment of the REEP1 gene in a biological sample, for use as the test sample in the assessment for the presence or absence of a polymorphism of interest. For example, in a representative embodiment, each of the exons of the REEP1 gene can be amplified.

The test sample is assessed to determine whether one or more mutations of interest in the REEP1 gene (polymorphisms of interest) are present in the REEP1 gene of the individual. In general, detecting a polymorphism of interest may be carried out by determining the presence or absence of nucleic acids containing the polymorphism of interest in the test sample. The polymorphism can be a change in the REEP1 gene, such as the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene; duplication of all or a part of the gene; transposition of all or a part of the gene; or rearrangement of all or a part of the gene. More than one such change may be present in a single gene. Such sequence changes cause a difference in the polypeptide encoded by the REEP1 gene. For example, if the difference is a frame shift change, the frame shift can result in a change in the encoded amino acids, and/or can result in the generation of a premature stop codon, causing generation of a truncated polypeptide. Alternatively, a polymorphism associated with a disease or condition or a susceptibility to a disease or condition associated with the REEP1 gene can be a synonymous alteration in one or more nucleotides (i.e., an alteration that does not result in a change in the polypeptide encoded by the REEP1 gene). Such a polymorphism may alter splicing sites, affect the stability or transport of mRNA, or otherwise affect the transcription or translation of the gene. A REEP1 gene that has any of the changes or alterations described above is referred to herein as an "altered REEP1 gene."

In a first method, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of the polymorphism of interest can be indicated by hybridization of nucleic acid in the genomic DNA, RNA, or cDNA to a nucleic acid probe. A "nucleic acid probe", as used herein, can be a DNA probe or an RNA probe; the nucleic acid probe can contain at least one polymorphism of interest, as described herein. The probe can be, for example, the gene, a gene fragment (e.g., one or more exons), a vector comprising the gene, a probe or primer, etc.

To detect one or more of the polymorphisms of interest, a hybridization sample is formed by contacting the test sample with at least one nucleic acid probe. A preferred probe for detecting mRNA or genomic DNA is a labeled nucleic acid probe capable of hybridizing to mRNA or genomic DNA of the REEP1 gene. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA or genomic DNA. The hybridization sample is maintained under conditions which are sufficient to allow specific hybridization of the nucleic acid probe to mRNA or genomic DNA of the REEP1 gene. "Specific hybridization", as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and REEP1 gene or mRNA in the test sample, the polymorphism that is present in the nucleic acid probe is also present in the REEP1 gene of the individual. More than one nucleic acid probe can also be used concurrently in this method. Specific hybridization of any one of the nucleic acid probes is indicative of the presence of polymorphism of interest, as described herein.

In Northern analysis (see Current Protocols in Molecular Biology, Ausubel, F. et al., eds., John Wiley & Sons, supra), the hybridization methods described above are used to identify the presence of a polymorphism of interest. For Northern analysis, a test sample comprising RNA is prepared from a biological sample from the individual by appropriate means. Specific hybridization of a nucleic acid probe, as described above, to RNA from the individual is indicative of the presence of a polymorphism of interest, as described herein.

For representative examples of use of nucleic acid probes, see, for example, U.S. Pat. Nos. 5,288,611 and 4,851,330.

Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P. E. et al., *Bioconjugate Chemistry*, 1994, 5, American Chemical Society, p. 1 (1994). The PNA probe can be designed to specifically hybridize to a REEP1 gene comprising one or more of the polymorphisms of interest described herein. Hybridization of the PNA probe to a REEP1 gene is indicative of the presence of the polymorphism of interest.

In another method of the invention, mutation analysis by restriction digestion can be used to detect a mutant REEP1 gene, or an REEP1 gene containing a polymorphism(s) of interest, if the mutation or polymorphism in the REEP1 gene results in the creation or elimination of a restriction site. A sample containing genomic DNA from the individual is used. Polymerase chain reaction (PCR) can be used to amplify all or a fragment of the REEP1 gene (and, if necessary, the flanking sequences) in the sample. RFLP analysis is conducted as described (see Current Protocols in Molecular Biology, supra). The digestion pattern of the relevant DNA fragment indicates the presence or absence of polymorphism in the REEP1 gene.

Direct sequence analysis can also be used to detect specific polymorphisms of interest in the REEP1 gene. A sample comprising genomic DNA or RNA is used, and PCR or other appropriate methods can be used to amplify all or a fragment of the REEP1 gene, and/or its flanking sequences, if desired. The sequence the REEP1 gene, or a fragment of the gene (e.g., one or more exons), or cDNA, or fragment of the cDNA, or mRNA, or fragment of the mRNA, is determined, using standard methods. The sequence of the gene, gene fragment, cDNA, cDNA fragment, mRNA, or mRNA fragment is compared with the known nucleic acid sequence of the REEP1 gene, cDNA or mRNA, as appropriate. The presence of a polymorphism of interest can then be identified.

Allele-specific oligonucleotides can also be used to detect the presence of a polymorphism of interest, through the use of dot-blot hybridization of amplified oligonucleotides with allele-specific oligonucleotide (ASO) probes (see, for example, Saiki, R. et al., (1986), Nature (London) 324:163-166). An "allele-specific oligonucleotide" (also referred to herein as an "allele-specific oligonucleotide probe") is an oligonucleotide of approximately 10-50 base pairs, preferably approximately 15-30 base pairs, that specifically hybridizes to the REEP1 gene, and that contains a polymorphism of interest as described herein. An allele-specific oligonucleotide probe that is specific for particular polymorphisms can be prepared, using standard methods (see Current Protocols in Molecular Biology, supra). To identify polymorphisms of interest, a sample comprising DNA is used. PCR can be used to amplify all or a fragment of the REEP1 gene, and its flanking sequences. The DNA containing the amplified REEP1 gene (or fragment of the gene) is dot-blotted, using standard methods (see Current Protocols in Molecular Biology, supra), and the blot is contacted with the oligonucleotide probe. The presence of specific hybridization of the probe to the amplified REEP1 is then detected. Specific hybridization of an allele-specific oligonucleotide probe to DNA from the individual is indicative of the presence of a polymorphism of interest.

In another embodiment of the invention, fluorescence resonance energy transfer (FRET) can be used to detect the presence of a polymorphism of interest. FRET is the process of a distance-dependent excited state interaction in which the emission of one fluorescent molecule is coupled to the excitation of another. A typical acceptor and donor pair for resonance energy transfer consists of 4-[[4-(dimethylamino)phenyl]azo]benzoic acid (DABCYL) and 5-[(2-aminoethylamino]naphthalene sulfonic acid (EDANS). EDANS is excited by illumination with 336 nm light, and emits a photon with wavelength 490 nxn. If a DABCYL moiety is located within 20 angstroms of the EDANS, this photon will be efficiently absorbed. DABCYL and MANS will be attached to two different oligonucleotide probes designed to hybridize head-to-tail to nucleic acid adjacent to and/or overlapping the site of one of the mutations of interest. Melting curve analysis is then applied: cycles of denaturation, cooling, and re-heating are applied to a test sample mixed with the oligonucleotide probes, and the fluorescence is continuously monitored to detect a decrease in DABCYL fluorescence or an increase in EDANS fluorescence (loss of quenching). While the two probes remain hybridized adjacent to one another, FRET will be very efficient. Physical separation of the oligonucleotide probes results in inefficient FRET, as the two dyes are no longer be in close proximity. The presence or absence of a mutation of interest can be assessed by comparing the fluorescence intensity profile obtained from the test sample, to fluorescence intensity profiles of control samples comprising known mutations of interest in the REEP1 gene.

In another embodiment, arrays of oligonucleotide probes that are complementary to target nucleic acid sequence segments from an individual, can be used to identify polymorphisms of interest. For example, in one embodiment, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, the entire teachings of each of which are incorporated by reference herein. Techniques for the synthesis of these arrays using mechanical synthesis methods are described in, e.g., U.S. Pat. No. 5,384,261, the entire teachings of which are incorporated by reference herein.

Once an oligonucleotide array is prepared, a nucleic acid of interest is hybridized with the array and scanned for polymorphisms. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence which includes one or more previously identified polymorphic markers is amplified by well known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detection of a single polymorphism, arrays can include multiple detection blocks, and thus be capable of analyzing multiple, specific polymorphisms. In alternate arrangements, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

Additional description of use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect polymorphisms of interest. Representative methods include direct manual sequencing (Church and Gilbert, (1988), *Proc. Natl. Acad. Sci. USA* 81:1991-1995; Sanger, F. et al. (1977) *Proc. Natl. Acad. Sci.* 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V. C. et al. (19891) *Proc. Natl. Acad. Sci. USA* 86:232-236), mobility shift analysis (Orita, M. et al. (1989) *Proc. Natl. Acad. Sci. USA* 86:2766-2770; Rosenbaum and Reissner (1987) *Biophys. Chem.*, 265:1275; Keen et al. (1991) *Trends Genet.*, 7:5; restriction enzyme analysis (Flavell et al. (1978) *Cell* 15:25; Geever, et al. (1981) *Proc. Natl. Acad. Sci. USA* 78:5081); heteroduplex analysis; chemical mismatch cleavage (CMC) (Cotton et al. (1985) *Proc. Natl. Acad. Sci. USA* 85:4397-4401); RNase protection assays (Myers, R. M. et al. (1985) *Science* 230:1242); use of polypeptides which recognize nucleotide mismatches, such as *E. coli* mutS protein (See, for example, U.S. Pat. No. 5,459,039); Luminex xMAP™ technology; and/or allele-specific PCR, for example.

These methods can be used to identify the presence of one or more mutations of interest in the REEP1 gene as described herein. For example, in certain embodiments, the methods can be used to assess the REEP1 gene of an individual for the presence of one or more polymorphisms of interest.

In one particular embodiment of the invention, the methods of assessing a test sample for the presence or absence of a mutation in the REEP1 gene, as described above, are used to assess an individual for the presence or absence of a genetic polymorphism associated with SPG. The presence of a mutation in the REEP1 gene, such as the presence of at least one of the mutations of interest (e.g., a single base transversion C→G at nucleotide 56 (56C→G); a single base transition C→A at nucleotide 59 (59C→A); a transition at nucleotide 182-2G→A (182-2G→A); a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14 (606+14C→T); a single base transition G→T in the 3'-UTR at 606+43 (606+43G→T); or a single base transition G→A in the 3'-UTR at 606+50 59C→A (606+50G→A)) is indicative of the presence of a genetic polymorphism associated with SPG.

In another embodiment of the invention, the methods of assessing a test sample for the presence or absence of a mutation in the REEP1 gene, as described above, are used to diagnose SPG in an individual. In these methods, the presence of a mutation in the REEP1 gene, such as the presence of at least one polymorphism of interest (e.g., a single base transversion C→G at nucleotide 56 (56 C→G); a single base transition C→A at nucleotide 59 (59C→A); a transition at nucleotide 182-2G→A (182-2G→A); a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14 (606+14C→T); a single base transition G→T in the 3'-UTR at 606+43 (606+43G→T); or a single base transition G→A in the 3'-UTR at 606+50 59C→A (606+50G→A)) is indicative of the presence of SPG.

The present invention also pertains to kits (e.g., reagent kits) useful in the methods of the invention. Such kits comprise components useful in any of the methods described herein, including for example, hybridization probes or primers (e.g., labeled probes or primers), reagents for detection of labeled molecules, restriction enzymes (e.g., for RFLP analysis), allele-specific oligonucleotides, means for amplification of nucleic acids comprising REEP1 or a fragment of REEP1, or means for analyzing the nucleic acid sequence of REEP1. For example, in one embodiment, the kit comprises components useful for analysis of mutations of interest using microsphere-based technology such as Luminex xMAP™ technology. In a preferred embodiment of the invention, the kit comprises components for detecting one or more of the mutations of interest (e.g., a single base transversion C→G at nucleotide 56 (56 C→G); a single base transition C→A at nucleotide 59 (59C→A); a transition at nucleotide 182-2G→A (182-2G→A); a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14 (606+14C→T); a single base transition G→T in the 3'-UTR at 606+43 (606+43G→T); or a single base transition G→A in the 3'-UTR at 606+50 59C→A (606+50G→A)).

The present invention is explained in greater detail in the following non-limiting exemplification.

EXAMPLIFICATION

Identification of Gene Underlying Familial Spastic Paraplegia

Linkage Study

A whole genome linkage screen was conducted on two independent families (DUK2299 and KUK2036). Two point and multi-point linkage analysis was performed using the VITESSE software package (O'Connell, J. R. and Weeks, D. E., *Nat. Genet.* 11:402-408 (1995)), assuming a disease allele frequency of 0.001. Allele frequencies of the markers were calculated from unaffected spouses in the families. Due to the incomplete penetrance of this disorder, an "affecteds-only" (low penetrance) model was used for the analysis. Mutations in the spastin and atlastin genes were excluded by sequencing analysis, as these two genes are the most frequently mutated in autosomal dominant SPG. Linkages to SPG3A, SPG5, SPG8, SPG10, SPG12, SPG13, and SPG19 chromosomal loci were specifically excluded by analysis of microsatellite markers.

A new SPG locus was identified on chromosome 2p12; a summary of two-point LOD scores for chromosome 2p12 candidate region is shown in Table 1.

TABLE 1

Summary of two-point LOD scores for chromosome 2p12 candidate region

|        | Family | $\Theta = 0.00$ | $\Theta = 0.05$ | $\Theta = 0.10$ | $\Theta = 0.15$ | $\Theta = 0.20$ | $\Theta = 0.30$ | $\Theta = 0.40$ |
|--------|--------|-------|-------|-------|-------|-------|-------|-------|
| D2S1777 | 2036  | 1.334 | 1.184 | 1.031 | 0.874 | 0.716 | 0.407 | 0.150 |
|        | 2299   | 3.365 | 3.073 | 2.768 | 2.448 | 2.113 | 1.388 | 0.597 |
|        | Total  | 4.698 | 4.257 | 3.798 | 3.322 | 2.829 | 1.795 | 0.746 |
| D2S139 | 2036   | 1.043 | 0.914 | 0.738 | 0.654 | 0.527 | 0.297 | 0.117 |

TABLE 1-continued

Summary of two-point LOD scores for chromosome 2p12 candidate region

| | Family | Θ = 0.00 | Θ = 0.05 | Θ = 0.10 | Θ = 0.15 | Θ = 0.20 | Θ = 0.30 | Θ = 0.40 |
|---|---|---|---|---|---|---|---|---|
| | 2299 | −0.929 | 1.180 | 1.260 | 1.205 | 1.087 | 0.739 | 0.297 |
| | Total | 0.115 | 2.094 | 2.043 | 1.858 | 1.614 | 1.036 | 0.414 |
| D2S289 | 2036 | 1.113 | 0.986 | 0.857 | 0.726 | 0.595 | 0.342 | 0.132 |
| | 2299 | 2.140 | 1.864 | 1.578 | 1.284 | 0.985 | 0.419 | 0.074 |
| | Total | 3.253 | 2.850 | 2.435 | 2.010 | 1.579 | 0.761 | 0.205 |
| D2S2951 | 2036 | 0.790 | 0.685 | 0.583 | 0.484 | 0.391 | 0.227 | 0.098 |
| | 2299 | 3.621 | 3.299 | 2.961 | 2.607 | 2.235 | 1.442 | 0.605 |
| | Total | 4.411 | 3.984 | 3.544 | 3.091 | 2.627 | 1.669 | 0.703 |
| TATA | 2036 | 0.672 | 0.584 | 0.499 | 0.418 | 0.341 | 0.205 | 0.093 |
| 112E03 | 2299 | 3.487 | 3.188 | 2.877 | 2.551 | 2.209 | 1.471 | 0.661 |
| | Total | 5.159 | 3.772 | 3.376 | 2.968 | 2.550 | 1.676 | 0.754 |

The combined two-point LOD score was 4.7 at marker D2S2951, and fine mapping with additional microsatellite markers narrowed the region to about 9 Mb between D2S139 and D2S2181. Markers D2S2951, D2S139 and D2S2181 are available through the STS database at NCBI. For marker D2S2951, see UniSTS 16507 and GenBank accession number G10313; for marker D2S139, see UniSTS 13780 or 55533, and GenBank accession number Z16777; for marker D2S2181, see UniSTS 33021 and GenBank accession number Z52418. This new form has been classified as SPG31.

Mapping of the Gene Underlying SPG31

Mutation screening was performed on nine candidate genes (CTNNA2, SUCLG1, TGOLN2, MATA2A, VAMP8, VAMP5, IMMT, VPS24, and REEP1). Genomic DNA was isolated from total blood samples obtained from SPG patients and control persons using standard extraction protocols. In the patients, the REEP1 mutation screening was performed by PCR-amplifying all 7 coding exons of REEP1 using intronic primers. The PCR products spanned 50 bp of flanking intronic sequence. PCR products were sequenced on an ABI3730 DNA Analyzer (Applied Biosystems Inc.) using the BigDye Terminator Cycle Sequencing Kit 3.1 (Applied Biosystems). The DNA sequence data were collected and analyzed using the ABI DNA Sequencing Analysis software 5.0 and the Sequencher package (Gene Codes Corp., USA). When a mutation was detected in an index person, additional family members, if available, were analyzed in order to determine co-segregation of the observed sequence variation with the disease. The numbering of the REEP1 codons was based upon the published amino acid sequence at NCBI (see, for example, Genbank accession number AY562239, submitted Nov. 26, 2004; GenBank accession number Q9H902, updated Jan. 24, 2006). For each detected mutations, 365 control samples (730 chromosomes) of European descent were screened. All mutations detected in SPG31 patients were not present in those controls.

Both linked families showed different missense mutations in the gene "receptor expression enhancing protein 1" (REEP1). REEP1 cDNA and the encoded protein are shown in Genbank accession number AY562239, as submitted on Nov. 26, 2004; the cDNA is also shown as SEQ ID NO: 1 in the Sequence Listing. The REEP1 gene product contains two transmembrane domains, a TB2/DP1 (deleted in polyposis) domain (TB2-DP1_HVA22), and a predicted extracellular C-terminal end as obtained by the conserved domain database at NCBI. See pfam03134 in the conserved domain data base at NCBI.

Family DUK2299 carried a single nucleotide deletion, 507delC, Gly169fs, which led to a frame shift and resulted in an extended protein. In KUK2036 a splice site mutation predicted to destroy the highly conserved acceptor (3') splice of exon 4, 182-2G→A, was identified. Both mutations co-segregated with the disease phenotype in these families and were not present in 366 healthy controls (732 chromosomes). The affected amino acid residues were highly conserved throughout different species, underscoring their functional significance. (To identify conserved regions, sequences from different species were derived from the Entrez protein database and aligned manually (data not shown).).

Frequency of SPG31

Identification of this gene underlying SPG31 allowed for mutation screening in independent SPG probands. A sample of 94 SPG cases was screened for mutations in REEP1, either isolated cases or probands from small pedigrees. These individuals had not been screened before for mutations in any the spastin and atlastin SPG genes. Other additional mutations were identified, including frame shift mutations; missense mutations; and three single nucleotide changes in the 5'-UTR of REEP1. all mutations were not present in either 366 healthy controls (732 chromosomes) or 492 controls. One frame shift mutation, 426delG, Gly181fs, occurred in exon 6 and led to the same frame shift observed in family DUK2299, above. A missense mutation, 59C→A, Ala20Glu, occurred in the conserved TB2_DP1_HVA22 domain of REEP1. Mutations like the mutations in the 5'-UTR of REEP1 are accepted to be of causative nature in autosomal dominant diseases (Ishikawa, K. et al., *Am. J. Hum. Genet.* 77:280-296 (2005)). A summary of the detected mutations in REEP1 is shown in Table 2.

TABLE 2

Detected Mutations in REEP1

| Family | Mutation | Exon | # Controls |
|---|---|---|---|
| ATH1 | 56 C→G, Pro→Arg | 2 | 492 |
| DUK2189 | 59C→A, Ala20Glu | 2 | 366 |
| DUK2036 | 182-2G→A, 5'-splice site, fs | 4 | 366 |
| ATH2 | 193delT (frame shift); | 4 | 492 |
| ATH3 | 223delC (frame shift) | 4 | 492 |

TABLE 2-continued

Detected Mutations in REEP1

| Family | Mutation | Exon | # Controls |
|---|---|---|---|
| DUK2299 | 507delC, Gly169fs | 6 | 366 |
| DUK2369 | 526delG, Gly181fs | 6 | 366 |
| ATH4 | 606 + 14C→T | 3'-UTR | 492 |
| DUK2354 | 606 + 43G→T | 3'-UTR | 366 |
| DUK1959 | 606 + 50G→A | 3'-UTR | 366 |

SUMMARY

The results of the experiment indicated a frequency of 6 out of 96 (6.2%) including the UTR mutations. Without the UTR mutations, the frequency is 4 out of 96 (4.2%). Either way, the new SPG gene REEP1 represents the third most common SPG gene, surpassed only by spastin (ca. 40%) and atlastin (ca. 10%).

While this invention has been particularly shown and described with references to preferred embodiments thereof, it will be understood by those skilled in the art that various changes in form and details may be made therein without departing from the spirit and scope of the invention as defined by the appended claims.

2. The method of claim 1, wherein the test sample from the individual comprises genomic DNA.

3. The method of claim 2, wherein the genomic DNA comprises chromosome 2 or a fragment thereof comprising 2p12.

4. The method of claim 1, wherein assessing the test sample comprises amplifying all or a fragment of the REEP1 gene.

5. The method of claim 1, wherein assessing the test sample comprises direct sequence analysis.

6. The method of claim 1, wherein the mutation is selected from the group consisting of: a single base transversion C→G at nucleotide 56 (56 C→G); a single base transition C→A at nucleotide 59 (59C→A); a transition at nucleotide 182-2G→A (182-2G→A); a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14 (606+14C→T); a single base transition G→T in the 3'-UTR at 606+43 (606+43G→T); and a single base transition G→A in the 3'-UTR at 606+50 59C→A (606+50G→A)).

7. A method of diagnosing hereditary spastic paraplegia (SPG) in an individual, the method comprising assessing a test sample from the individual for the presence of at least one mutation in the receptor expression enhancing protein 1 (REEP1) gene, wherein the presence of at least one mutation is indicative of the presence of hereditary spastic paraplegia.

8. The method of claim 7, wherein the test sample from the individual comprises genomic DNA 9. The method of claim 8, wherein the genomic DNA comprises chromosome 2 or a fragment thereof comprising 2p12. .

What is claimed is:

1. A method of assessing an individual for the presence or absence of a genetic polymorphism associated with hereditary spastic paraplegia (SPG), the method comprising assessing a test sample from the individual for the presence of at least one mutation in the receptor expression enhancing protein 1 (REEP1) gene, wherein the presence of at least one mutation is indicative of the presence of a genetic polymorphism associated with hereditary spastic paraplegia.

10. The method of claim 7, wherein assessing the test sample comprises amplifying all or a fragment of the REEP1 gene.

11. The method of claim 7, wherein assessing the test sample comprises direct sequence analysis.

12. The method of claim 7, wherein the mutation is selected from the group consisting of: a single base transversion C→G at nucleotide 56 (56 C→G); a single base transition C→A at nucleotide 59 (59C→A); a transition at nucleotide 182-2G→A (182-2G→A); a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14 (606+14C→T); a single base transition G→T in the 3'-UTR at 606+43 (606+43G→T); and a single base transition G→A in the 3'-UTR at 606+50 59C→A (606+50G→A)).

13. A method of assessing a test sample from an individual for the presence or absence of a genetic polymorphism associated with hereditary spastic paraplegia (SPG), the method comprising determining the nucleic acid sequence of the receptor expression enhancing protein 1 (REEP1) gene or a fragment thereof, and assessing the sequence for one or more mutations in the receptor expression enhancing protein 1 (REEP1) gene, wherein the presence of at least one mutation is indicative of the presence of a genetic polymorphism associated with hereditary spastic paraplegia.

14. The method of claim 13, wherein the mutation is selected from the group consisting of: a single base transversion C→G at nucleotide 56 (56 C→G); a single base transition C→A at nucleotide 59 (59C→A); a transition at nucleotide 182-2G→A (182-2G→A); a single base deletion of nucleotide 193 (193delT); a single base deletion of nucleotide 223 (223delC); a single base deletion of nucleotide 507 (507delC); a single base deletion of nucleotide 526 (526delG); a single base transition C→T in the 3'-UTR at 606+14 (606+14C→T); a single base transition G→T in the 3'-UTR at 606+43 (606+43G→T); and a single base transition G→A in the 3'-UTR at 606+50 59C→A (606+50G→A)).

15. The method of claim 13, wherein determining the nucleic acid sequence comprises hybridization of a probe to all or a fragment of the REEP1 gene sequence to determine the presence or absence of one or more mutations of interest.

16. The method of claim 15, wherein determining the nucleic acid sequence comprises hybridization of two or more probes to all or fragments of the REEP1 gene sequence to determine the presence or absence of two or more mutations of interest.

17. The method of claim 13, wherein determining the nucleic acid sequence comprises using a probe array to detect target nucleic acid sequence segments to identify the presence or absence of one or more mutations of interest in the REEP1 gene sequence.

18. The method of claim 13, wherein assessing the test sample comprises sequencing all or a fragment of the REEP1 gene in the test sample.

19. The method of claim 13, wherein determining the nucleic acid sequence comprises amplifying all or a fragment of the REEP1 gene.

20. The method of claim 19, wherein assessing the test sample comprises sequencing all or a fragment of the REEP1 gene in the test sample.

* * * * *

```
SEQUENCE LISTING

<160> NUMBER OF SEQ ID NOS: 1

<210> SEQ ID NO 1
<211> LENGTH: 606
<212> TYPE: DNA
<213> ORGANISM: Homo Sapiens

<400> SEQUENCE: 1
atggtgtcat ggatcatctc caggctggtg gtgcttatat ttggcaccct ttaccctgcg     60
tattattcct acaaggctgt gaaatcaaag gacattaagg aatatgtcaa atggatgatg    120
tactggatta tatttgcact tttcaccaca gcagagacat tcacagacat cttcctttgt    180
tggtttccat tctattatga actaaaaata gcatttgtag cctggctgct gtctccctac    240
acaaaaggct ccagcctcct gtacaggaag tttgtacatc ccacactatc ttcaaaagaa    300
aaggaaatcg atgattgtct ggtccaagca aaagaccgaa gttacgatgc ccttgtgcac    360
ttcgggaagc ggggcttgaa cgtggccgcc acagcggctg tgatggctgc ttccaaggga    420
cagggtgcct tatcggagag actgcggagc ttcagcatgc aggacctcac caccatcagg    480
ggagacggcg cccctgctcc ctcgggcccc ccaccaccgg ggtctgggcg ggccagcggc    540
aaacacggcc agcctaagat gtccaggagt gcttctgaga gcgctagcag ctcaggcacc    600
gcctag                                                               606
```